US00H002223H

(19) United States
(12) Statutory Invention Registration
Brizzolara

(10) Reg. No.: US H2223 H
(43) Published: Sep. 2, 2008

(54) PATTERNED, MICROMETER-SIZED ANTIBODY FEATURES

(75) Inventor: Robert A. Brizzolara, Bethesda, MD (US)

(73) Assignee: The United States of America as represented by the Secretary of the Navy, Washington, DC (US)

(21) Appl. No.: 10/406,197

(22) Filed: Apr. 4, 2003

Related U.S. Application Data

(60) Provisional application No. 60/394,872, filed on Jul. 11, 2002.

(51) Int. Cl.
*G01N 33/00* (2006.01)

(52) U.S. Cl. ..... 422/56; 422/57; 422/68.1; 422/82.01; 436/501; 436/518; 436/527; 436/528; 435/4; 435/7.1; 435/283.1; 435/287.1; 435/287.2

(58) Field of Classification Search ..... 422/56, 422/57, 68.1, 82.01; 436/501, 518, 527, 528; 435/4, 7.1, 283.1, 287.1, 287.2, 287.9
See application file for complete search history.

(56) References Cited

U.S. PATENT DOCUMENTS

| | | | | |
|---|---|---|---|---|
| 4,591,570 | A | 5/1986 | Chang | |
| 4,724,318 | A | 2/1988 | Bennig | |
| 5,120,662 | A | 6/1992 | Chan et al. | |
| 5,143,854 | A | 9/1992 | Pirrung et al. | |
| 5,158,869 | A | 10/1992 | Pouletty et al. | |
| 5,252,743 | A | 10/1993 | Barrett et al. | |
| 5,356,785 | A | 10/1994 | McMahon et al. | |
| 5,384,261 | A | 1/1995 | Winkler et al. | |
| 5,447,837 | A | 9/1995 | Urnovitz | |
| 5,451,683 | A | 9/1995 | Barrett et al. | |
| 5,482,867 | A | 1/1996 | Barrett et al. | |
| 5,545,531 | A | 8/1996 | Rava et al. | |
| 5,677,196 | A | 10/1997 | Herron et al. | |
| 5,807,522 | A | 9/1998 | Brown et al. | |
| 5,858,801 | A | 1/1999 | Brizzolara | |
| 5,919,712 | A | 7/1999 | Herron et al. | |
| 6,235,541 | B1 * | 5/2001 | Brizzolara | 436/518 |
| 6,406,921 | B1 * | 6/2002 | Wagner et al. | 436/518 |
| 6,573,369 | B2 * | 6/2003 | Henderson et al. | 536/23.1 |
| 2003/0068446 | A1 * | 4/2003 | Mirkin et al. | 427/430.1 |
| 2004/0037959 | A1 * | 2/2004 | Mirkin et al. | 427/256 |
| 2005/0009092 | A1 * | 1/2005 | Brennan | 435/6 |

OTHER PUBLICATIONS

Stryer, Lubert, "Molecular Design of Life", Biochemistry Fourth Edition, W.H. Freeman and Company, New York, pp. 60–63 (1995).

Alberte, Randall S., "Biosensor Technologies: Perspectives and Promise", Naval Research Reviews, pp. 2 & 3.

Lutwyche, M.I. Despont, M., Drechsler, U., Durig, U., Haberle, W., Rothuizen, H., Stutz, R., Widmer, R., Binnig, G.K. and Vettiger P., "Highly Parallel Data Storage System Based on Scanning Probe Arrays", Applied Physics Letters, vol. 77, No. 20, pp. 3299–3301, Nov. 13, 2000.

(Continued)

*Primary Examiner*—Dan Pihulic
(74) *Attorney, Agent, or Firm*—Jane Barrow

(57) ABSTRACT

A biosensor has a micrometer sized antibody substrate surface which may include patterned single or multiple antibody substrates. The substrate is capable of detecting multiple chemical species simultaneously and/or continuously monitoring a single chemical species.

15 Claims, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

OTHER PUBLICATIONS

Binnig, G., Quate, C.F., and Gerber, Ch. "Atomic Force Microscope"Physical Review Letters, vol. 56, No. 9, pp. 930–933 Mar. 3, 1986.

Brizzolara, Robertr A., "Patterning Multiple Antibodies on Polystyrene", Biosensors & Bioelectronics 15 (2000) pp. 63–68.

Pohl, D.W., Fischer, U. Ch., and Durig, U.T., Scanning Near–Field Optical Microscopy (SNOM), Journal of Microscopy, vol. 152, Pt. 3, Dec. 1988, pp. 853–861.

Hengsakul, Manchumas and Cass, Anthony E.G., "Protein Patterning with a Photoactivatable Derivative of Biotin", Bioconjugate Chem. 1996, vol. 7, No. 2, pp. 249–254.

Pritchard, David John, Morgan, Hywel and Cooper Jonathan Mark, "Micron–Scale Patterning of Biological Molecules", Angew, Chem. Int. Ed. Engl. 1995, vol. 34 No. 1, pp. 91–93.

Sundberg, Steven A., Barrett, Ronald W., Pirrung, Michael, Lu, Amy L., Kiangsoontra, Benjang, and Holmes, Christopher P., "Spatially–Addressable Immobilization of Macromolecules on Solid Supports", J. Am. Chem. Soc. 1995, vol. 117, No. 49, pp. 12050–12057.

Conrad, David W., Davis, Anna V., Golightley, Sara K., Bart, John C. and Ligler, Frances S., "Photoactivatable Silanes for the Site Specific immobilization of Antibodies", SPIE, vol. 2978, pp. 12–21.

Ligler, Frances S., Conrad, David W., Golden, Joel P., Feldstein, Mark J., MacCraith, Brian D., Balderson, Stephanie D., Czarnaski, Joe and Rowe, Chris A., "Array Biosensor for Multi–Analyte Sensing", SPIE, vol. 3258, pp. 50–55.

Kimura, J., Kawana Y. and Kuriyama T., "An Immobilized Enzyme Membrane Fabrication Method Using an Ink Jet Nozzle", Biosensors 4, (1988), Elsevier Science Publishers Ltd, England, pp. 41–52.

Fodor, Stephen P.A., Read, J. Leighton, Pirrung, Michael C., Stryer, Lubert, Lu, Amy Tsai and Solar Dennis, "Light–Directed, Spatially Addressable Parallel Chemical Synthesis", Research Article, Science, vol. 251, pp. 767–773, Feb. 15, 1991.

Avramescu, Adrian, Ueta, Akio, Uesugi, Katsuhiro and Suemune, Ikuo, "Atomic Force Microscope Lithography on Carbonaceous Films Deposited by Electron–Beam Irradiation", Applied Physics Letters, vol. 72, No. 6, Feb. 9, 1998, pp. 716–718.

Park, S.W., Soh, H.T., Quate C.F. and Park S.–I., "Nanometer Scale Lithography at High Scanning Speeds with the Atomic Force Microscope Using Spin on Glass", Applied Physics Letters, vol. 67, No. 16, Oct. 16, 1995, pp. 2415–2417.

Held, R., Heinzel, T., Studerus, P., Ensslin K. and Holland, M., "Semiconductor Quantum Point Contact Fabricated by Lithography with an Atomic Force Microscope", Applied Physics Letters, vol. 71, No. 18, Nov. 3, 1997, pp. 2689–2691.

Bouchiat V. and Esteve D., "Lift–off Lithography Using an Atomic Force Microscope", Applied Physics Letters, vol. 69, No. 20, Nov. 11, 1996, pp. 3098–3100.

Sohn L.L. and Willett, R.L., "Fabrication of Nanostructures Using Atomic–Force–Microscope–Based Lithography", Applied Physics Letters, vol. 67, No. 11, Sep. 11, 1995, pp. 1552–1554.

Piner, Richard D., Zhu, Jin, Xu, Feng, Hong, Seunghun and Mirkin, Chad A., "Dip–Pen" Nanolithography, Research Article, Science, vol. 283, Jan. 29, 1999, pp. 661–663.

Freemantly, Michael, "Chemical Analysis and Synthesis on Microchips Promise a Variety of Potential Benefits", Science/technology, C&EN, Feb. 22, 1999, pp. 27–36.

Catt, K.J. and Tregear, G.W., "Solid–Phase Radioimmunoassay in Antibody–Coated Tubes", Science, vol. 158, Dec. 22, 1967, pp. 1570–1572.

Lee, Jin Ho, Kopecek, Jindrich and Andrade Joseph D., "Protein–Resistant Surfaces Prepared by PEO–containing Block Copolymer Surfactants", Journal of Biomedical Materials Research, vol. 23, pp. 351–368, (1989).

Eigler, D.M. and Schweizer E.K., "Positioning Single Atoms with a Low Temperature Scanning Tunneling Microscope", Nature, vol. 344, Apr. 5, 1990, pp. 524–526.

* cited by examiner

PATTERNED, MICROMETER-SIZED ANTIBODY FEATURES

CROSS-REFERENCE TO RELATED APPLICATION

This application claims the benefit of U.S. Provisional Application No. 60/394,872 filed Jul. 11, 2002, entitled "Patterned, Micrometer-sized Antibody Features", incorporated herein by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

1. Field of the Invention

The present invention relates micrometer scaled mono-analyte and multi-analyte substrates used in biosensors, including immunosensors, for environmental monitoring and medical diagnostic purposes.

2. Brief Description of the Related Art

Antibody substrates for use in biosensors or immunosensors have been described in U.S. Pat. Nos. 5,858,801 and 6,235,541, both to Robert A. Brizzolara and entitled "Patterning Antibodies on a Surface", the disclosure of each patent is herein incorporated by reference.

SUMMARY OF THE INVENTION

The present invention includes a biosensor subsystem comprising an antibody substrate having at least one micrometer scaled antibody pattern and means for interrogating such micrometer scaled antibody pattern.

The present invention also includes a process for producing a micrometer scaled antibody patterned substrate comprising the steps of coating an antibody-adsorbent substrate with an antibody-resistant material that is resistant to adsorption of antibodies, removing a micrometer scaled portion of the antibody-resistant material to produce a bare site on the antibody-adsorbent substrate having a micrometer scaled size, shape, and location on the substrate, adsorbing molecules of a selected antibody on to the bare site on the antibody adsorbent-substrate and rinsing the substrate to remove unadsorbed antibody molecules.

Additionally, the present invention includes an array biosensor comprising the biosensor subsystem.

BRIEF DESCRIPTION OF THE DRAWINGS

A more complete appreciation of the invention and many of its attendant advantages will be readily appreciated as the same becomes better understood by reference to the following detailed description when considered in connection with the accompanying drawing wherein.

DETAILED DESCRIPTION OF THE PREFERRED EMBODIMENT

The present invention includes a biosensor subsystem for chemical analysis, a process for producing a micrometer scaled antibody patterned substrate and an array biosensor that includes the biosensor subsystem. The biosensor subsystem has antibody substrate comprising at least one micrometer scaled antibody pattern and a means for interrogating the antibody substrate, such as a transducer. The system preferably includes a micro-fluidic system and, when used for analysis of air samples, a cyclone separator. The antibody substrate may include a single antibody pattern, or a plurality of differing antibody patterns. The biosensor has reduced size and weight characteristics of conventional antibody-based biosensors, either for detecting single or multiple analytes, while maintaining specificity and high sensitivity. The present invention may perform single or multiple real-time and simultaneous and/or sequential immunoassay tests.

Patterning antibodies onto a surface in sub-micrometer features, as described herein, provides a reliable, cost-effective method for high resolution patterning of antibodies onto a chip supporting the substrate for development of the array biosensor. Antibody patterning refers to the defined spatial localization of antibody molecules on a surface, referred to herein as a patterned antibody, area or feature. As such, a patterned antibody feature, or multiple patterned antibody features, may be lithographically placed onto a specified substrate.

Figure 1:
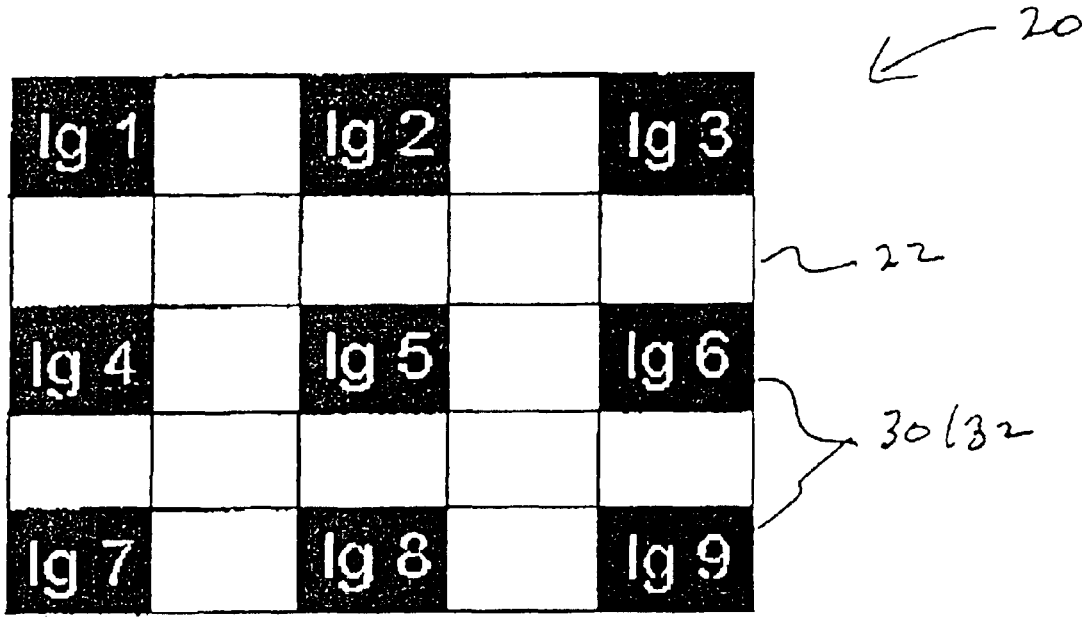
FIG. 1 is a schematic of an array of the present invention useful in a microfabricated, multi-analyte biosensor.

As seen in the schematic representation of FIG. 1, the substrate 20 of the present invention has multiple micrometer scaled antibody patterns 30, represented by different antibodies Ig1 to Ig9, placed into the surface 22 which may be at the micrometer and/or sub-micrometer size. These patterns include one or more micrometer scaled areas of antibodies. 32 on the substrate 20. A single patterned area 30 incorporates a single antibody. Multiple micrometer scaled antibody patterns may contain a single, i.e., identical, antibodies or differing antibodies, i.e., at least two of the micrometer scaled antibody patterns comprise different antibodies. Preferably, there are from about two different antibody patterns to about nine different antibody patterns on a given substrate. The plurality of micrometer scaled antibody patterns may be configured in any appropriate orientation for functionally enabling the biosensor subsystem to properly work, such as a checker pattern, concentric circles, line arrangements, etc., with the proper selection of the configuration determinable by one of ordinary skill in the art in light of the disclosure herein. Such determination may be generally influenced by such factors as spacing size relative to the proposed detected antigen, available space on the substrate, number of patterns desired, types of antigens to be detected, desired response time of the biosensor, and other like factors known to those skilled in the art. Preferably each feature contains an antibody to a different antigen, with avoidance of cross contamination of the antibodies through spacing between the different individual antibody patterns. The micrometer scale antibody pattern more preferably includes void spaces about equal to or greater than the size of the antibody spaces to minimize any overlap or interference between patterns. The micrometer scaled antibody pattern on the substrate permits multiple chemical species to be detected with a single device simultaneously, with test results of the device read and evaluated automatically.

The patterning method of the present invention fabricates patterns at the micrometer and sub-micrometer scaled sizes, such as from about 100 μm or less, 50 μm or less, 10 μm or less, and 1 μm or less (i.e., 100,000 nm or less, 50,000 nm or less, 10,000 nm or less, and 1000 nm or less, respectively). Preferably the scaled sized range from about 500 nm or less, such as the size of a single antibody molecule, e.g., approximately 15 nm, more preferably from about 250 nm to about 10 nm, and most preferably from about 100 nm to about 50 nm for multi-antibody chips. Additionally, the present invention fabricates patterns from about 500 nm or less, such as from about 250 nm to about 10 nm, more preferably from about 100 nm to about 50 nm for single-antibody chips. Micrometer-scaled sizes of antibody features of the multiple-antibody sensor result in significant reductions in size, weight, and power consumption for the array biosensor device, and permit the microfabrication of the antibody array. The substrates possessing two different antibodies disclosed herein include antibody features with dimensions typically as small as 10 μm, and for substrates possessing one antibody feature sizes as small as 0.5 μm.

Combinatorial arrays may be employed to detect a single chemical species using different antibodies having different affinities for the target chemical, resulting in a wider range of response times and reset times. The response time of the biosensor array is controlled by the binding affinity of the antibody, such as a high affinity antibody giving a relatively fast response time and a low affinity antibody giving a relatively slow response time. However, the high affinity antibody retains a relatively slow reset time after a detection cycle because of the longer time required for the biosensor to unload or release the analyte for the antibodies to be available to bind new analyte. With combinatorial arrays having variable affinities, the biosensor retains the capability for tracking concentration gradients of the analyte.

The antibody substrate is formed onto the substrate that forms a part of a chip and comprises a solid surface. The antibody-adsorbent substrate may be composed of any material conventionally used to physically adsorb proteins or antibodies, preferably in a spontaneous, physical process. Preferably, a hydrophobic material suitable for this purpose is used, such as polystyrene or polypropylene. More preferably the hydrophobic surface includes, in part or whole, polystyrene. An advantage of using the polystyrene substrate is that it uses physisorption of the antibodies to the surface, rather than a covalent linkage. Thus, the immobilization and patterning are inherently simpler and faster. However, many other hydrophobic polymeric materials such as polyethylene or copolymers of polyethylene and polypropylene will also work well. The use of cross-linking agents or other chemical agents to chemically bind the antibodies to the substrate are generally not used.

Figure 2:
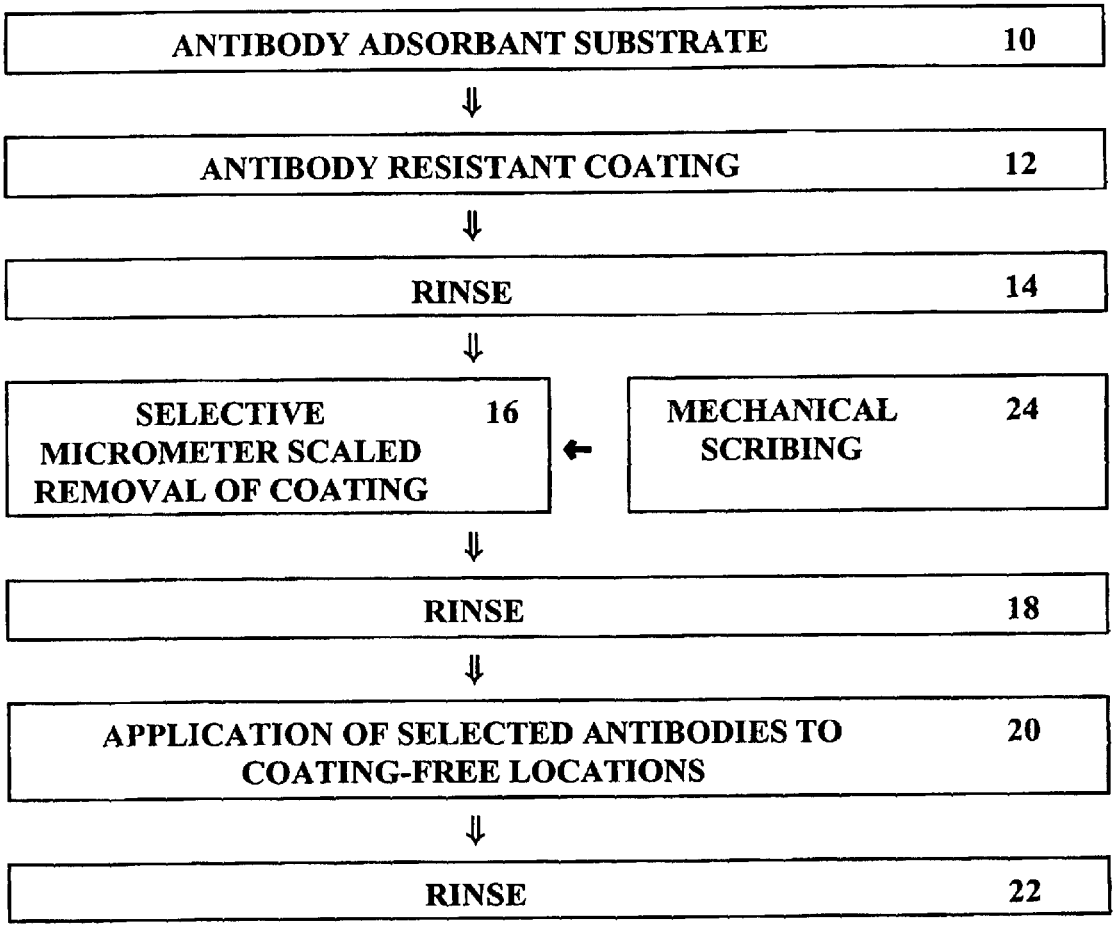
FIG. 2 is block diagram of the micrometer scaled antibody patterning fabrication process of the present invention.

The process for producing a micrometer scaled antibody patterned substrate, diagramed in FIG. 2, includes the steps of coating an antibody-adsorbent substrate with an antibody-resistant material that is resistant to adsorption of antibodies, removing a micrometer scaled portion of the antibody-resistant material to produce a bare site on the antibody-adsorbent substrate having a precise micrometer scaled size, shape, and location on the substrate, adsorbing molecules of a selected antibody on to the bare site on the antibody adsorbent-substrate and rinsing the substrate to remove unadsorbed antibody molecules. When different antibody patterns are placed into a single substrate, the process of removing, adsorbing and rinsing sufficient for applying two or more antibody substrates, may be repeated.

As seen in FIG. 2, an antibody adsorbent substrate 10, such as a polystyrene substrate having an approximate dimension of 10 mm×5 mm, initially undergoes a surface coating step 12 with an antibody resistant material, e.g., bovine serum albumin (BSA), by immersion of the substrate in a 1% w/v solution of the BSA at room temperature for approximately 30 minutes. This is followed by step 14 for a rinse, such as in phosphate buffered saline (PBS) for 2 hours at a temperature of 37° C. The BSA coating is then selectively removed from discrete micrometer scaled locations on the substrate surface in accordance with coating removal step 16, followed by another PBS rinse step 18 before application of selected antibodies in parallel to coating free locations on the substrate in accordance with step 20. The process is completed by a contamination preventing rinse in deonized water as step 22. Significantly the coating removal step 16, which is physical or mechanical in nature as a result of the use of a micro-stylus for mechanical scribing 24 for forming micrometer scaled patterns.

The patterning of single and multiple antibodies may be accomplished by sequential patterning of the multiple antibodies on a single substrate. Alternatively, inkjet printing or micropipeting may be used for patterning many antibodies in parallel resulting in faster device fabrication times while increasing the number of different areas to be patterned on a given substrate.

For example, the serial process used for producing a multiple antibody patterned substrate may include (1) coating an antibody-adsorbent substrate with an antibody-resistant material, (2) removing a portion of the antibody-resistant material by mechanical scribing to produce a bare site on the antibody-adsorbent substrate having a precise micrometer size, shape, and location on the substrate, (3) adsorbing molecules of a selected antibody on to the bare site on the antibody-adsorbent substrate, (4) rinsing the substrate to remove unadsorbed antibody molecules, and (5) coating the antibody-adsorbent substrate with more of the antibody-resistant material to cover the bare surface of the substrate between the newly adsorbed antibody molecules for single antibody patterns, with the additional step of (6) repeating steps (2) through (5) until each of the antibodies has been adsorbed at its specific site on the antibody-adsorbent substrate for multiple antibody patterns.

Parallel processing for multiple antibody patterned substrates may include (1) coating an antibody-adsorbent substrate with an antibody-resistant material that is resistant to the adsorption of antibodies, (2) simultaneously removing portions of the antibody-resistant material by mechanical scribing to produce bare sites on the antibody-adsorbent substrate having precise micrometer sizes and shapes and each site having a precise location which corresponds to a specific antibody, (3) adsorbing molecules of each antibody to its specific bare site on the antibody-adsorbent substrate, (4) rinsing the substrate to remove unadsorbed antibodies, and (5) coating the antibody-adsorbent substrate with more of the antibody-resistant material to cover the bare surface of the substrate between the adsorbed antibody molecules.

Coatings that resists adsorption of antibodies (antibody-resistant coatings) on the hydrophobic surface and that can be scribed away at the micrometer scaled are applicable for use in the present invention. Examples of preferred antibody-resistant coatings include (1) bovine serum albumin, (2) gelatin, (3) lysozyme, (4) octoxynol, (5) polysorbate 20, and (6) polyethylene oxide-containing block copolymer surfactants. Octoxynol can be represented by the formula $CH_3C(CH_3)_2CH_2C(CH_3)_2$—Ar—$O(CH_2CH_2O)_n$—-H, wherein n is preferably from 9 to 10 and Ar represents a aryl unit. The antibody-resistant polyethylene oxide-containing block copolymer surfactants include those containing polyethylene oxide-polypropylene oxide copolymer blocks and those containing polyethylene oxide-polybutylene oxide copolymer block. These surfactants are discussed by Jin Ho Lee et al. In "Protein-resistant surfaces prepared by PEO-containing block copolymer surfactants", *Journal of Biomedical Materials Research*, Vol. 23, pp.

351–368 (1989), herein incorporated by reference in its entirety. The more preferred antibody-resistant coatings are bovine serum albumin, gelatin, and lysozyme, with bovine serum albumin being the most preferred. Polystyrene surfaces bind antibody molecules through hydrophobic interactions, but the BSA coating inhibits the adsorption of antibody to a surface.

Figure 3:
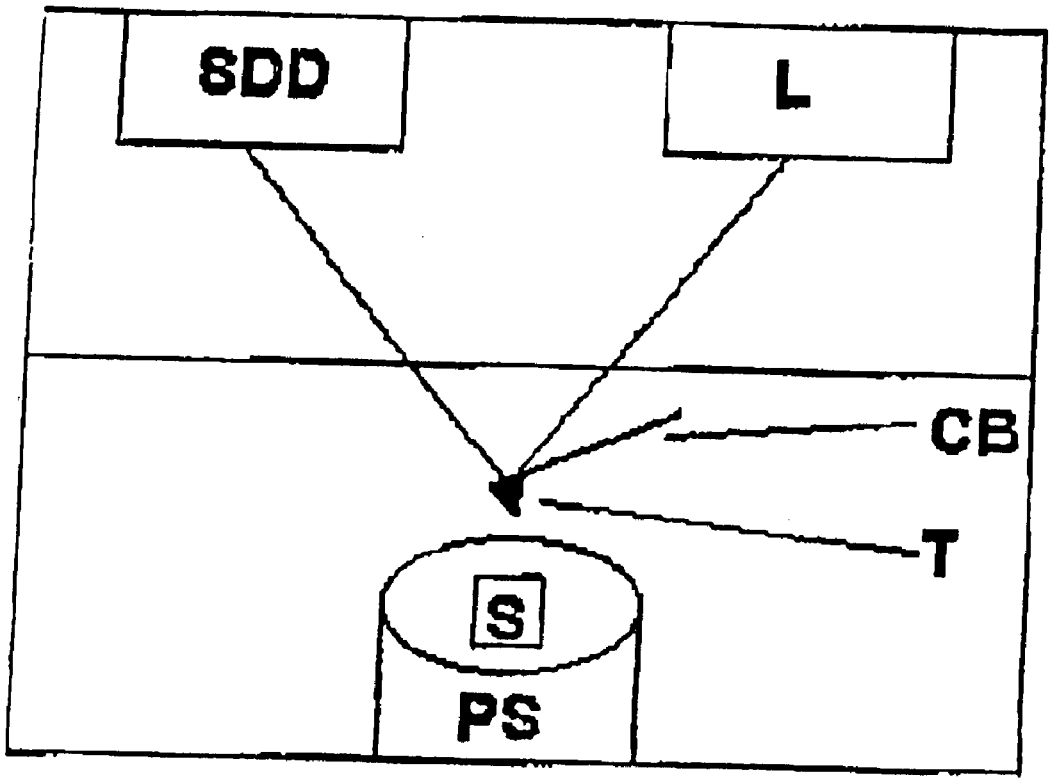
FIG. 3 is a schematic of the operation of the Atomic Force Microscope in a scribing mode useful in the present invention; and, FIG. 4 is a schematic of the biosensor of the present invention showing the patterned antibody chip, transducer and microfluidic system.

A high precision coating remover, either as a process or device, is used to remove the antibody-resistant coating. The high precision coating remover removes the antibody-resistant coating in defined spatial areas with sufficiently high spatial resolution for micrometer scaled definition. A preferred high precision coating remover comprises the Atomic Force Microscope (abbreviated herein as "AFM"). The Atomic Force Microscope allows a cost-effective method of patterning antibodies onto the substrate with high spatial resolution using precise force control between the stylus and substrate. The Atomic Force Microscope is used to fabricate small antibody features, such as multiple features containing different antibodies on the same substrate. The Atomic Force Microscope is commercially available and manufactured by Digital Instruments of Santa Barbara, California. Microfabricated Atomic Force Microscope arrays have been disclosed in M. Lutwyche, M. Despont, U. Drechsler, U. Durig, W. Haberle, H. Rothuizen, R. Stutz, R. Widmer, G. Binnig, P. Vettiger, "Highly Parallel Data Storage System Based on Scanning Probe Arrays," Applied Physics Letters, vol. 77, no. 20, p. 3299–3301, 13 Nov. 2000, the disclosure of this article is incorporated herein by reference. As a lithographic tool, the Atomic Force Microscope is capable of exacting precision, such as 40 nm, 30 nm or 20 nm, and is particularly applicable for patterning sub-micrometer antibody features on a chip, such as 0.1 nm spatial resolution and conceivably patterning individual antibody molecules, e.g., 15 nm. The use of mechanical scribing, such as by the Atomic Force Microscope, eliminates the necessity of lithographic masks and the resulting registration and alignment issues. Mechanical scribing also avoids the vacuum requirement associated with ion beam sputtering, as described in U.S. Pat. Nos. 5,858,801 and 6,235,541 (Brizzolara). In one alternative embodiment to solution-based adsorption, the Atomic Force Microscope, or use of Scanning Tunneling Microscopy (abbreviated herein as "STM") is used to position individual antibody molecules within the patterns The Atomic Force Microscope is depicted schematically in FIG. 3. As seen in FIG. 3, the Atomic Force Microscope works by using an atomically sharp tip (T) that is mounted on a cantilever beam (CB). The (T) tip is located above the sample (S) to be imaged. Using the precision stepper motor built into the Atomic Force Microscope, the tip (T) is slowly lowered toward the sample (S) until it makes contact. The tip-sample loading force for an Atomic Force Microscope operating in imaging mode in the ambient atmosphere is typically $10^{-6}$ to $10^{-8}$ N. The combination of the small loading force and sharp tip results in a precise contact area, such as a few nanometers. The tip (T) is rastered over the sample surface by moving the sample (S) using a piezoelectric scanner (PS). The cantilever beam deflects in response to surface topography. A laser (L) and a split diode detector (SDD) are used to measure the amount of canti lever beam deflection. A plot of the cantilever beam deflection as a function of the tip=s position on the sample surface yields a topographic map of the surface. This topographic map is of extremely high spatial resolution, for example, a few nm, because of the small tip-sample contact area and the high precision (<1nm) with which the piezoelectric scanner (PS) can position the tip (T) on the sample surface. Using such an operation, the Atomic Force Microscope mechanically removes selected areas of coating, such as BSA, exposing the underlying hydrophobic substrate, such as a polystyrene substrate. However, for scribing, the high precision motor of the Atomic Force Microscope is used to move the tip (T) several micrometers downwards toward the sample (S), so that the tip-sample loading force is increased above the $10^{-6}$ to $10^{-8}$ N usually used for imaging which causes the tip (T) to penetrate through the layer of BSA to the polystyrene substrate surface. The feedback circuit that controls the height of the tip above the sample surface is disabled by setting the integral and proportional gains to zero, so that the Atomic Force Microscope does not withdraw the tip (T) from the sample (S) during patterning. While the tip (T) is embedded in the layer of BSA, it is scanned in a raster pattern that removes the layers of BSA. Scanning the tip (T) from about five to about twenty frames over a given area of the BSA generally removes the BSA layer from a polystyrene substrate. Controllable parameters for Atomic Force Microscope patterning of the BSA layer include the distance of tip (T) movement and the scan rate. The tip (T) was generally found to be lowered toward the sample (S) a greater distance to effectively remove BSA from larger areas with the scan rate decreased for larger patterned areas to maintain an approximately constant tip velocity.

The means for interrogating the micrometer scaled antibody pattern includes any appropriate mechanism for registering a bound antibody to the substrate. Detection of the labeled antigens comprises sufficient spatial resolution for micrometer scale readings. Preferably, the means for interrogating includes a transduction system. Systems that can serve as a transduction system are available commercially with the specific form of the transduction system depends on the conjugate label that is used. In it simplest form, the transduction system includes benchtop analysis equipment such as a microscope. The transduction system may include, without limitation, optical or force transduction means, such as an Atomic Force Microscope, microscope, fluorescence microscope, scanning mirror optics, and the like. Preferably, the Atomic Force Microscope is used in an imaging mode to interrogate the micrometer scaled antibody pattern. Other methods of detecting the labeled antigen (interrogating the microfabricated antibody features and determining how much antigen has been bound by these features) may include for example a Charge-Coupled Device (CCD) in combination with a lens system, a Scanning Near-field Optical Microscope (SNOM), or an Atomic Force Microscope in indentation mode. For example, an atomic force microscope was used as the transduction system in imaging 10 nm gold particles that were used as the label (see e.g., Example 3 herein). A fluorescence microscope was used as the transduction system in imaging a fluorescent label (see e.g., U.S. Pat. No. 6,235,541 to Brizzolara). Preferably, the transduction system is microfabricated and integrated on the same chip as the micropattemed antibody array and the microfluidics system. Microfabricated transducers may also include an array of atomic force microscope cantilevers (see e.g., M. Lutwyche, M. Despont, U. Drechsler, U. Durig, W. Haberle, H. Rothuizen, R. Stutz, R. Widmer, G. Binnig, P. Vettiger, Appl. Phys. Lett. 2000, 77, 3299), or a Scanning Near Field Optical Microscope (see e.g., D. Pohl, U. Fischer, U. Durig, J. Microsc. 1988, 152, 853. and E. Betzig, P. Finn, J. Weiner, Appl. Phys. Lett. 1992, 60, 2484).

Use of a transduction method for detecting the antibody-antigen binding event addresses the transduction of signals from the small length scales from the microfabricated antibody features of the present invention. The Atomic Force Microscope may be used to image gold nanoparticle labels that are conjugated to an antigen as part of a competitive assay. Preferably image analysis software is used to count the gold nanoparticles in each antibody nanostructure following a competition assay and a pattern-matching scheme employed to identify the analyte. In a competition assay, the number of gold nanoparticles bound to the substrate is inversely proportional to the analyte concentration, providing a quantitative measure of each analyte (the species to be detected) concentration and allowing a fast, sensitive and selective chemical detection capability. Alternatively, the Atomic Force Microscope may be used as a nanoindenter, interrogating the elastic modulus of the various antibody nanostructures. Coverage of an antibody nanostructure by gold nanoparticles changes the elastic modulus of that nanostructure relative to a nanostructure coated with antibody but with no gold nanoparticles. The transduction method using the Scanning Near-Field Optical Microscopy, manufactured by Digital Instruments of Santa Barbara, California under the tradename Aurora NSOM optically interrogates antibody nanostructures patterned on a substrate. The Scanning Near-Field Optical Microscopy includes a sharpened optical fiber tip that is brought close, such as approximately 10 nm, to the sample surface. The optical fiber detects light reflected or transmitted from the sample, or it can illuminate the surface.

Gold particle labels are preferably used. Alternatives to the gold particle labels, such as fluorophores, chromophores or other such labeling means as determinable by one skilled in the art, may be used to provide labels that are detectable with sufficiently high spatial resolution for micrometer scale reading.

The multiple antibody patterned substrates of this invention function as multiple analyte or antigen capturing structures that are suitable for automatic analysis. Each analyte is identified by the position (site) of the antibody that captures it on the substrate. Conventional radioactive, fluorescent, or enzymatic labels can be used to mark the captured analytes for detection and measurement. The amount of radioactivity, intensity of fluorescence, or quantity of enzymatic reaction product (color change) is proportional to the quantity of the specific analyte captured by the specific antibody at the specific site. The quantity of analyte capture will be proportional to the concentration of the analyte present in the test environment (solution, air, blood, water, etc.) and the quantity of the capturing antibody present on the substrate at that site. The quantity of the antibody is controlled by the conditions under which the antibody was originally adsorbed on the antibody-adsorbent substrate and by the area of bare substrate available for antibody adsorption. The intensity of the label signals from the various sites on the substrate provides a complete picture of the concentrations of the analytes found in the test environment.

An array biosensor incorporates the biosensor subsystem as a component part therein. The array biosensor may be part of a system for chemical analysis. The system for chemical analysis includes the array biosensor (having an antibody substrate having at least one micrometer scaled antibody pattern and means for interrogating such micrometer scaled antibody pattern, such as a transducer) together with a microfluidic system. As such, in additional to being integrated with transduction device, the mono- or multi-analyte, microfabricated biosensor chip may further be integrated with a microfluidics system as a means of delivering the proper reagents to the chip to perform the immunoassay. Systems that deliver reagents to a chip are available commercially. In the simplest form, the fluidics system include the reagents being manually pipetted onto the chip at the appropriate times. Preferably the fluidic system is automated. An additional, preferred attribute is microfabrication of the automated fluidics system. These microfluidics systems are available commercially from, without limitation for example, Aclara of Mountain View, Calif., Caliper of Newton, Mass., Orchid Biosciences of Princeton, N.J., and Cepheid of Sunnyvale, Calif. and may be adapted for this purpose. Preferably, the microfluidics system are integrated onto the same chip as the micropatterned antibody array. Other microfluidics systems include, without limitation for example, Hewlett-Packard's "lab-on-a-chip" technology (see e.g., M. Freemantle, Chemical and Engineering News, Feb. 22, 1999, p. 27; the disclosure of which is herein incorporated by reference). The addition of a microfluidic systems to integrate analytical capabilities onto the chip include high through put, use of small amounts of materials and reagents, low manufacturing, operating and maintenance costs and low power consumption. Miniaturization additionally enables the fielding micrometer scaled chemical detection capabilities in remote and/or small sensing equipment with microfabrication of these sensors and the ability to integrate them onto micro-electro-mechanical (MEMS) devices being preferred for their deployment, such as in unmanned airborne vehicles (UAV). The array biosensor of the present invention may include an automated sensor capable of detecting multiple chemical species and tracking their concentrations in space and time.

Figure 4:
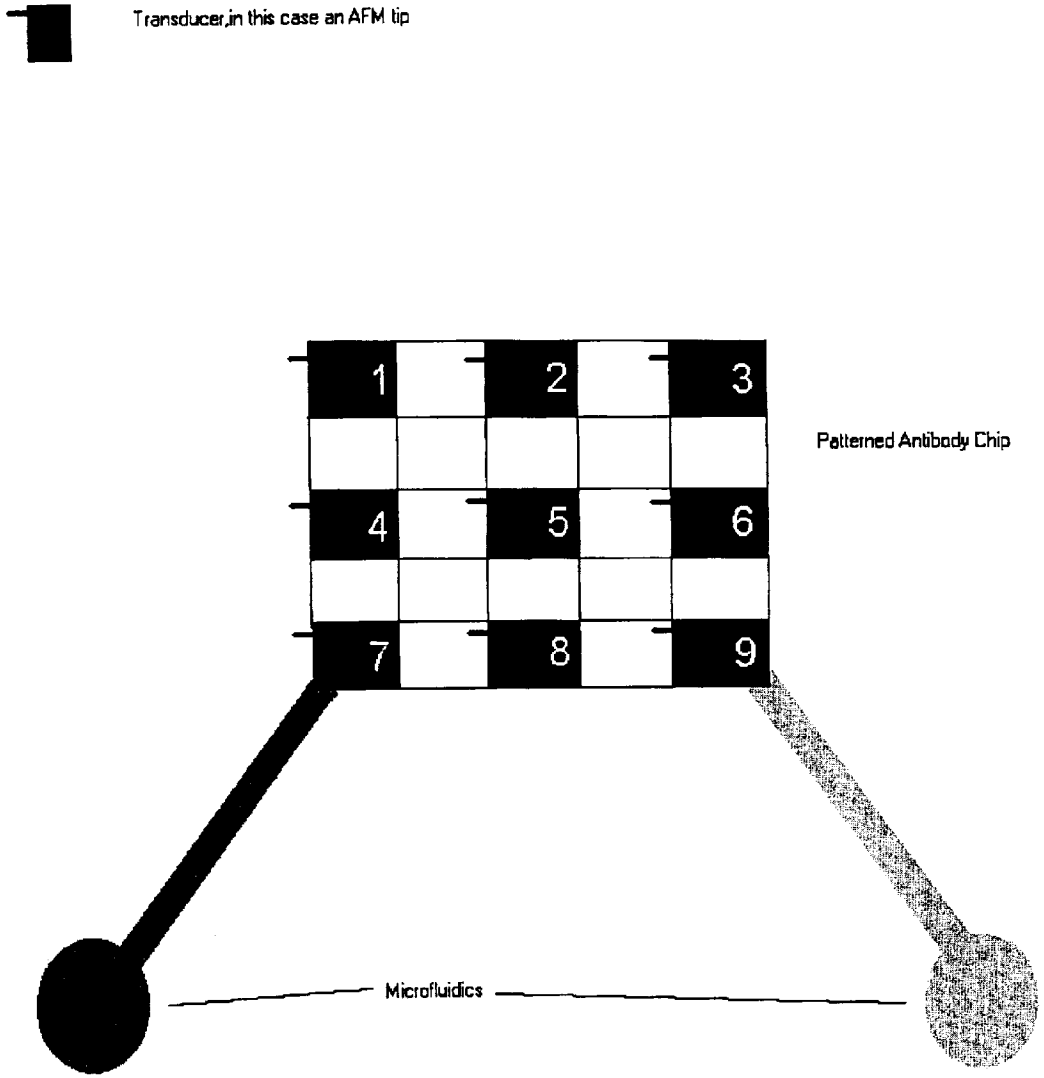

As seen in FIG. 4, the micropatterned antibody array chip is preferably used in a biosensor by using it with a microfluidic system that delivers the appropriate reagents to the chip at the appropriate time, and a transduction system, such as a transducer, that reports a signal when the chip detects an antigen at any one of several sites, represented by numbers 1 through 9. Preferably, all three components are microfabricated and integrated on the same chip. In addition, for monitoring of air samples, a device for entraining the air sample in water, such as a cyclone separator is used.

The biosensing device of the present invention may include (A) an analyte-capturing structure comprising (1) an antibody-adsorbent substrate, (2) one or more antibodies adsorbed to the substrate, wherein the one or more antibodies are located at a specific micrometer scaled sites on the substrate apart from other antibodies, and (3) an antibody-resistant material covering the substrate between the adsorbed molecules of the antibodies for immobilization thereof at discrete locations, and (B) means for determining the types and quantities of the analytes captured by the antibodies.

Microfabricating a bioscnsor chip with multiple areas patterned with different antibodies provides a multifunctional biosensor chip for single-use applications in environmental monitoring, chemical-biological warfare agent detection, and medical monitoring. As such, array biosensors of the present invention are applicable for maritime uses such as monitoring wastewater outflow of ships or water quality of water treatment facilities to ensure environmental compliance and proper functioning of filtration or treatment systems, as well as monitoring minuscule contaminants in a water sample, such as very small oil concentrations in water. Array biosensors may be placed in condition-based maintenance applications, such as for example, in an inaccessible area of a ship to monitor for the presence of a corrosion product, or hazardous and potentially hazardous areas, such as for example, used in locations for detecting chemical/biological warfare agents or other contaminants. Uses of the array biosensors in the medical field, include for example, monitoring the bloodstream for the presence of specific hormones, toxins, etc.

The use of the sensor with multiple antibodies patterned onto it as an array biosensor has several advantages that include the ability to detect multiple chemical species with a single device instead of using a separate device for each chemical species, to detect single chemical species with different antibodies having different binding affinities allowing the sensor to have a range of response and reset times, and to automate the multi-antibody array biosensor when combined with an appropriate means of transduction.

To use this microfabricated biosensor to assess a liquid sample, a volume of the sample is added to one of the reservoirs of the microfluidics system by the operator. A solution of antigen conjugated with a label is added to a second reservoir. The device is then be placed in automated mode, and performs a standard immunoassay, using the antibody array (see e.g., E. Harlow and D. Lane, "Antibodies: A Laboratory Manual", Cold Spring Harbor Laboratory Press, Cold Spring Harbor, NY.). The microfluidics system immerses the antibody array in a mixture of the sample and the antigen conjugate. If the sample contains the antigen, this antigen competes for antibody binding sites with the antigen-conjugate in the patterned antibody region(s) that are specific to that antigen. Once the system has reached equilibrium, the fluidics system rinses the antibody array, removing unbound antigen and antigen-conjugate. The transduction system then automatically assesses the quantity of antigen conjugate present in each antibody region. This quantity is inversely proportional to the amount of antigen present in the sample.

The array biosensor of the present invention includes multiple antibodies on a substrate to perform multiple, real-time and simultaneous immunoassay tests. The array biosensor employs a plurality of antibodies, each specific to a different chemical species (analyte), and each immobilized onto a different site or feature on a single chip. The array biosensor allows detection of multiple analytes with a single device. This capability allows the tracking of chemical gradients in space and time, and detecting extremely small analyte concentrations.

EXAMPLE 1

Antibodies G4018 (anti-goat IgG, whole molecule, Sigma Chemical Company, St. Louis, Mo.) and C2288 (anti-chicken IgG, whole molecule, Sigma Chemical Company, St. Louis, Mo.) were patterned onto a polystyrene surface. G4018 is an antibody developed in rabbit that is specific to (binds) goat antibody. The antigen was G7652 (anti-Mouse IgG, whole molecule, gold [10 nm] conjugate), Sigma Chemical Company, St. Louis, Mo.). This is an antibody developed in goat that is specific to mouse antibody, and is conjugated to a 10 nm gold nanoparticles that can be visualized using an Atomic Force Microscope. With functionally capable G4018 immobilized on the surface, it will specifically bind G7652. C2288 is an anti-chicken antibody developed in rabbit, thus it does not bind G7652. C2288 is used as a control in place of G4018 in some of the experiments described below, to check for non-specific adsorption of G7652 (adsorption caused by something other than antibody-antigen binding). The G4018, C2288, and G7652 were diluted 1:3 in phosphate-buffered saline (PBS).

Polystyrene samples were coated with bovine serum albumin (BSA) by immersing them in 1% w/v BSA in PBS solution at room temperature for approximately 30 minutes. The G4018, C2288 and G7652 immersions were performed at 37° C. for approximately two hours. Excessive incubation times may promote non-specific binding. Several small tissues soaked in deionized water were placed in the covered polystyrene dishes with the samples during incubation to maintain a humid atmosphere and prevent drying of the antibody solution. G4018, C2288, G7652 and BSA immersions were all followed by a brief rinse in deionized water to remove unbound antibody from the substrate. The samples were dried using flowing nitrogen. G4018 and C2288 immersions were followed by a BSA immersion to block the surface, with the blocking step followed by a rinse in deionized water to remove unbound BSA and a drying step with flowing nitrogen.

Mechanical patterning of selected areas on BSA coated substrates was accomplished using an atomic force microscope (Digital Instruments NanoScope II) with a J-head as a lithographic tool to remove the BSA coating in a selected area, exposing the polystyrene substrate. This produced a surface with differential affinity for antibodies. When the sample was immersed in antibody solution, antibodies adsorbed to the polystyrene, but not to the BSA-coated areas. After the Atomic Force Microscope tip was used to selectively remove BSA from the polystyrene surface, the sample was rinsed in deionized water and immersed in a solution of the first antibody for approximately two hours at approximately 37° C. The sample was then rinsed in deionized water and dried under flowing nitrogen. It was then immersed in BSA solution for approximately 30 minutes at room temperature to "block" the surface, i.e., the BSA molecules covered any remaining areas of exposed polystyrene to prevent antibody adsorption in undesired areas. The sample was then rinsed, dried and placed in the Atomic Force Microscope to remove BSA from a second selected area of the sample surface (exposing the underlying polystyrene substrate). After the BSA was removed from the second selected area, the sample was immersed in a solution of the second antibody for approximately two hours at approximately 37° C. The sample was then rinsed in deionized water and dried, and immersed in BSA solution for approximately 30 minutes at room temperature (blocking the surface). This resulted in two areas on the substrate patterned with two separate antibodies. Additional patterned antibody areas are possible on the sample by repeating the above procedure.

The fabricated working array biosensor can detect two different antigens. The specific compounds depend on which antibodies are used. Although the present example exemplifies antibodies that bind other antibodies, the technique may be used to detect any antigenic chemical compound or biological material. Fabrication techniques preferably are generally tailored to ensure that the antibodies are present in the patterned areas of the surface and not present in undesired areas, and that the antibodies have retained their functionality throughout the patterning process.

EXAMPLE 2

Two test samples were fabricated to verify that antibody G4018 binds G7652 and that antibody C2288 does not bind G7652. The Atomic Force Microscope can be used to detect the difference. Both test samples used substrates that were approximately 0.5 cm ×0.5 cm polystyrene substrates. The entire surface of one substrate was coated with G4018, and the entire surface of the other substrate was coated with C2288. The G4018 coated surface, after incubation in a solution of G7652/gold-labeled antibody, showed the gold label uniformly covering the surface. The C2288 coated surface, after incubation in a solution of G7652/gold-labeled antibody, showed a non-uniform sparse indications of nanoparticles on the surface. The gold nanoparticles appeared larger than 10 nm in the AFM images because the radius of curvature of the end of the Atomic Force Microscope tips is approximately 20 nm to 50 nm. These results were confirmed using x-ray photoelectron spectroscopy (XPS) to measure the gold concentration on the surface of each sample. The G4018 showed a gold atomic concentration of approximately 0.31% and the C2288 showed a gold atomic concentration of approximately 0.01%. The XPS results showed a factor of 31 more gold on the G4018 surface than on the C2288 surface, confirming the Atomic Force Microscope results.

EXAMPLE 3

A polystyrene substrate, Sample 1, was patterned with six features in accordance with the procedure described in Example 1. The parameters for patterning are shown in Table 1, below:

TABLE 1

Parameter for patterning Sample 1

| Feature | Feature Size (μm) | X position (μm) | Y position (μm) | Scan Rate (lines/sec) | Number of Scans | Tip Distance toward sample (μm) |
|---|---|---|---|---|---|---|
| 1 | 10 | 0 | 30 | 19.53 | 10 | 18 |
| 2 | 10 | 0 | 0 | 19.53 | 10 | 15 |
| 3 | 20 | 0 | −39 | 19.53 | 10 | 20 |
| 4 | 10 | −20 | 30 | 19.53 | 10 | 15 |
| 5 | 10 | −20 | 0 | 19.53 | 10 | 10 |
| 6 | 20 | −20 | −39 | 19.53 | 10 | 15 |

Sample 1 demonstrated the capability of the Atomic Force Microscope to pattern multiple antibody areas on a substrate. Sample 1 had two different antibodies patterned on it. The BSA was selectively removed from three specific areas on the substrate (Features 1, 2, and 3) using the Atomic Force Microscope, with the patterning parameters for Sample 1 are given in Table 1. C2288 antibody was immobilized in these three regions. Subsequently, BSA was selectively removed from Features 4, 5 and 6 from this sample and antibody G4018 immobilized in these three Regions. All other areas on the substrate remained covered with BSA.

As a working biosensor Sample 1 was designed to detect the G7652 (gold labeled) antibody. The sample was immersed in a solution of the antigen, G7652 for two hours at 37° C. Since G7652 shows specificity for only G4018, the G7652 was expected to be bound by the antibodies in features 4, 5, and 6, but not by the C2288 antibody in features 1, 2 and 3. The Atomic Force Microscope was used to image the sample and detect the presence or absence of gold particles in the patterned areas. Atomic Force Microscope images of the surface of Sample 1 showed a much concentration of gold particles in the G4018 patterned areas than in the C2288 patterned areas.

EXAMPLE 4

A polystyrene substrate, Sample 2, was patterned with six features in accordance with procedure described in Example 1. The parameters for patterning are shown in Table 2, below:

TABLE 2

Parameter for patterning Sample 2

| Feature | Feature Size (μm) | X position (μm) | Y position (μm) | Scan Rate (lines/sec) | Number of Scans | Tip Distance toward sample (μm) |
|---|---|---|---|---|---|---|
| 1 | 10 | 0 | 30 | 19.53 | 10 | 15 |
| 2 | 10 | 0 | 0 | 19.53 | 10 | 10 |
| 3 | 20 | 0 | −39 | 19.53 | 10 | 15 |
| 4 | 10 | −15 | 30 | 19.53 | 10 | 15 |
| 5 | 10 | −15 | 0 | 19.53 | 10 | 10 |
| 6 | 20 | −15 | −39 | 19.53 | 10 | 15 |

Sample 2 had the same two antibodies patterned onto it as Sample 1, but the order of antibody immobilization was reversed. This was done to verify that the first antibody patterned onto the surface retains its functionality during the second patterning step. The Atomic Force Microscope parameters used in patterning the features on Sample 2 are detailed in Table 2, above.

As in Sample 1, Sample 2 demonstrated the capability of the Atomic Force Microscope to pattern multiple antibody areas on a substrate. Sample 2 had two different antibodies patterned on it. The BSA was selectively removed from three specific areas on the substrate (Features 4, 5, and 6) using the Atomic Force Microscope, with the patterning parameters for Sample 2 are given in Table 2. G4018 antibody was immobilized in these three regions. Subsequently, BSA was selectively removed from Features 1, 2 and 3 from this sample and antibody C2288 immobilized in these three regions. All other areas on the substrate remained covered with BSA.

As a working biosensor Sample 2 was designed to detect the G7652 (gold labeled) antibody. The sample was immersed in a solution of the antigen, G7652 for two hours at 37° C. Since G7652 shows specificity for only G4018, the G7652 was expected to be bound by the antibodies in features 4, 5, and 6, but not by the C2288 antibody in features 1, 2 and 3. The Atomic Force Microscope was used to image the sample and detect the presence or absence of gold particles in the patterned areas. Atomic Force Microscope images of the surface of Sample 2 showed a much higher concentration of gold particles in the G4018 patterned areas than in the C2288 patterned areas.

Images for Sample 2 were similar to the AFM images for Sample 1, with the G4018 patterned areas containing gold particles, and the C2288 regions containing very few gold particles, evidencing a higher concentration of gold particles in the G4018 patterned areas than the C2288 patterned areas. Samples 1 and 2 showed that for both cases the C2288 and G4018 antibodies Retained their functionality during patterning and that the gold particles in the G40 18 patterned areas results from binding of the G7652 antigen, and not to nonspecific adsorption. Additionally Samples 1 and 2 together showed that both of the samples have two, different, functional antibodies patterned onto them, with an antibody feature size as small as 10 μm .

EXAMPLE 5

One antibody, G4018 antibody, was patterned onto a polystyrene substrate with feature sizes including 500 nm, identified as Sample 3. Table 3, below, details the Atomic Force Microscope parameters:

TABLE 3

Parameters for patterning single antibody features on a substrate

| Feature | Feature Size (μm) | X position (μm) | Y position (μm) | Scan Rate (lines/sec) | Number of Scans | Tip Distance toward sample (μm) |
|---|---|---|---|---|---|---|
| 1 | 0.5 | −35 | 0 | 78.13 | 10 | 5 |
| 2 | 1 | −31 | 0 | 39.06 | 10 | 5 |
| 3 | 5 | −11 | 0 | 26.04 | 10 | 5 |

Sample 3 contained Features 1, 2 and 3, with Feature 1 approximately 500 nm ×1 μm, Feature 2 approximately 1 μm×1 μm and Feature 3 approximately 5 mm×5 μm. AFM imaging of Features 1 and 2 showed gold particles clearly visible in these features, from specific binding of G7652 antigen by G4018 antibody. A lower density of gold particles was visible outside the features, evidencing some gold particles nonspecifically adsorbed to G7652. The patterning showed a single antibody on a substrate of areas as small as 500 nm.

The foregoing summary, description, examples and drawings of the invention are not intended to be limiting, but are only exemplary of the inventive features which are defined in the claims.

What is claimed is:

1. A biosensor subsystem, comprising:

an antibody substrate having at least one micrometer scaled antibody pattern; and, means for interrogating said micrometer scaled antibody pattern.

2. The biosensor subsystem of claim 1, wherein the at least one micrometer scale antibody pattern comprises a size of from about 500 nm or less.

3. The biosensor subsystem of claim 2, wherein the at least one micrometer scale antibody pattern comprises a size of from about 250 nm to about 10 nm.

4. The biosensor subsystem of claim 3, wherein the at least one micrometer scale antibody pattern comprises a size of from about 100 nm to about 50 nm.

5. The biosensor subsystem of claim 1, wherein the at least one micrometer scale antibody pattern comprises a single antibody substrate.

6. The biosensor subsystem of claim 5, further comprising a plurality of micrometer scaled antibody patterns having a single antibody substrate.

7. The biosensor subsystem of claim 1, further comprising a plurality of micrometer scaled antibody patterns wherein at least two of the micrometer scaled antibody patterns comprise different antibody substrates.

8. The biosensor subsystem of claim 7, wherein the plurality of antibody substrates comprises from about 2 antibody substrates to about 9 antibody substrates.

9. The biosensor subsystem of claim 7, wherein the plurality of micrometer scaled antibody patterns comprise a checker pattern.

10. The biosensor subsystem of claim 1, wherein the at least one micrometer scaled antibody pattern comprises a spacing relative to the proposed detected antigen.

11. The biosensor subsystem of claim 1, wherein the at least one micrometer scaled antibody pattern comprises void spaces about equal to or greater than the size of the antibody spaces.

12. The biosensor subsystem of claim 1, wherein the antibody substrate comprises a hydrophobic substrate.

13. The biosensor subsystem of claim 12, wherein the hydrophobic substrate comprises polystyrene.

14. The antibody substrate of claim 1, wherein the means for interrogating comprises a transducer.

15. An array biosensor comprising the biosensor subsystem of claim 1.

* * * * *